United States Patent
De Lacharriere et al.

(10) Patent No.: US 6,169,069 B1
(45) Date of Patent: Jan. 2, 2001

(54) THERAPEUTIC/COSMETIC COMPOSITIONS COMPRISING CGRP ANTAGONISTS FOR TREATING THE EYES OR EYELIDS

(75) Inventors: Olivier De Lacharriere, Paris; Lionel Breton, Versailles, both of (FR)

(73) Assignee: Societe L'Oreal S.A., Paris (FR)

(*) Notice: Under 35 U.S.C. 154(b), the term of this patent shall be extended for 0 days.

(21) Appl. No.: 08/623,576

(22) Filed: Mar. 28, 1996

(30) Foreign Application Priority Data

Mar. 28, 1995 (FR) .................................. 95 03629

(51) Int. Cl.[7] .................................. A61K 38/00
(52) U.S. Cl. .................................. 514/2; 514/844
(58) Field of Search .................................. 514/2, 844

(56) References Cited

PUBLICATIONS

NeuroScience vol. 48, No. 4. pp.963–968. Buckley et al, 1992.*

Neuroscience, vol. 48, No. 4, Jun. 1992, pp. 963–968, Buckley et al.*

Neuroscience Letters, vol. 102, No. 2.3, Jul. 31, 1989, pp. 257–260, Louis et al.*

British Journal of Pharmacology, vol. 110, No. 2, 1993, pp. 772–776, Escott et al.*

British Journal of Pharmacology, vol. 104, No. 3, Nov. 1991, pp. 738–742, Hughes et al.*

* cited by examiner

*Primary Examiner*—Zohreh Fay
(74) *Attorney, Agent, or Firm*—Burns, Doane, Swecker & Mathis, L.L.P.

(57) ABSTRACT

Ocular and/or palpebral pruritus and/or ocular and/or palpebral pain and/or ocular and/or palpebral dysaesthesia afflicting a mammalian, notably human patient, are therapeutically treated by administering to such patient a therapeutically/cosmetically effective amount of at least one CGRP antagonist, advantageously in combinatory immixture with at least one antagonist of a neuropeptide other than CGRP, e.g., a substance P antagonist, and/or at least one inflammation mediator antagonist; the subject compositions are also well suited for making up and/or caring for human eyes, eyelashes and/or eyelids, especially sensitive eyes and eyelids.

5 Claims, No Drawings

THERAPEUTIC/COSMETIC COMPOSITIONS COMPRISING CGRP ANTAGONISTS FOR TREATING THE EYES OR EYELIDS

CROSS-REFERENCE TO COMPANION APPLICATIONS

Applications Ser. No. 08/592,529, filed Jan. 26, 1996, now U.S. Pat. No. 6,019,967 and Ser. No. 08/620,806, now U.S. Pat. No. 5,932,215 and Ser. No. 08/620,850, now U.S. Pat. No. 5,935,586 both filed concurrently herewith, and each assigned to the assignee hereof.

BACKGROUND OF THE INVENTION

1. Technical Field of the Invention

The present invention relates to the formulation of an antagonist of CGRP (peptide derived from the calcitonin gene: Calcitonin Gene Related Peptide, or "CGRP") into pharmaceutical compositions, in particular for topical application, for the treatment of ocular and/or palpebral pruritus and/or pain and/or dysaesthesias.

This invention also relates to the formulation of a CGRP antagonist into cosmetic compositions intended for making up or caring for the eyes or eyelids, as well as to a regimen for making up and/or caring for sensitive eyes.

2. Description of the Prior Art

It is known to this art that certain patients suffer from ocular and/or palpebral pain following operations or blows received to the eye. Moreover, and although the precise cause is not known, certain individuals very often experience sensations of itching or pruritus and dysaesthesic sensations around the eyes and eyelids. These may also be pruritus or dysaesthesic sensations of allergic origin.

By the term "dysaesthesic sensations" are intended sensations of burning or heating, stinging, tingling, discomfort and tightness. These sensations may be combined with redness.

All of these ophthalmic indications may, moreover, be combined with rosacea and possibly with conjunctivitis.

Among the factors triggering ophthalmic or palpebral pruriginous or dysaesthesic afflictions, exemplary thereof are rapid temperature variations, heat and in particular exposure to ultraviolet or infrared radiation, low relative humidity, exposure to violent winds or to currents of air (blowing machine, conditioned air), the application of surfactants, exposure to toxic or irritant vapors (solvents) or to dusts, irritant ophthalmological drops or topical products, irritant dermatological or cosmetic palpebral topical products (alpha-hydroxy acids, retinoids) or the use of certain cosmetics, even when these are not known to be particularly irritating.

Other factors triggering ocular or palpebral pruriginous or dysaesthesic afflictions which should also be included are allergens such as, in particular, pollen, animal hairs, acarians and molds.

Hitherto, the pathological mechanism of these signs was very poorly understood and ocular and/or palpebral dysaesthesias were treated with corticoids and also local antiseptics as an ophthalmic ointment or as drops.

Although corticoids are relatively effective at alleviating the above symptoms, they unfortunately have side effects which are often very severe, such as atrophies. Furthermore, they sensitize towards mycotic or bacterial infections and their kinetics are often slow (several minutes to a few hours). Moreover, their chronic use may lead to a pharmacodependency.

Thus, serious need continues to exist in this art for a treatment of the aforesaid ocular and palpebral dysaesthesias, pains and pruritus which does not have the above drawbacks/disadvantages.

SUMMARY OF THE INVENTION

A major object of the present invention is the administration of one or more CGRP antagonists to a mammalian, notably human patient, for treating the disease states indicated above.

CGRP is a polypeptide chemical species produced and released by a nerve ending. CGRP is involved, in particular, in respiratory and inflammatory diseases, in allergic diseases and in certain dermatological diseases such as eczema and prurigo.

It has now unexpectedly been determined that it is possible to treat ocular and/or palpebral pruritus and/or ocular and/or palpebral pain and/or ocular and/or palpebral dysaesthesias by preventing the synthesis and/or the release and/or the binding of CGRP.

Thus, the present invention features the formulation of at least one CGRP antagonist into a pharmaceutical or dermatological composition for treating ocular and/or palpebral pruritus and/or ocular and/or palpebral pain and/or ocular and/or palpebral dysaesthesias.

This invention also features the application of compositions containing one or more CGRP antagonists to the eyes or the eyelids to effect a marked reduction or even complete disappearance of the ophthalmic pruritus, dysaesthesic sensations and pain; a preventive and curative, calming and soothing effect on the eyes and eyelids is very rapidly attained, and in any event much more rapidly than with corticoids. In addition, no pharmacodependency results.

Too, this invention also features formulating these CGRP antagonists into cosmetic compositions for sensitive eyes and, in particular, lotions for cleansing or removing makeup from the eyes, and into makeup products for sensitive eyes and, especially, eye shadows, mascaras, eye pencils or eyeliners for sensitive eyes.

Thus, the present invention features the formulation of at least one CGRP antagonist into a cosmetic composition containing a cosmetically acceptable medium, such composition being intended for sensitive eyes.

The present invention accordingly features a regimen for making up or caring for sensitive eyes, comprising topically applying a cosmetic composition containing at least one CGRP antagonist, in a cosmetically acceptable medium, to the eyelids, the eyelashes and/or under the eyes.

This invention also features cosmetic, dermatological and/or pharmaceutical compositions for sensitive eyes, comprising an effective amount of at least one CGRP antagonist, in a cosmetically, pharmaceutically or dermatologically acceptable medium.

DETAILED DESCRIPTION OF BEST MODE AND SPECIFIC/PREFERRED EMBODIMENTS OF THE INVENTION

More particularly according to the present invention, the subject compositions comprise a cosmetically, pharmaceutically or dermatologically acceptable medium (vehicle, carrier or diluent), namely, a medium which is compatible with the skin and the eyes. The compositions containing the CGRP antagonist or antagonists are preferably administered via topical application. They may also be ingested or injected (systemic administration).

By "CGRP antagonist" is intended any molecule, whether organic or inorganic, which is capable of effecting inhibition of the receptor binding of CGRP or of effecting an inhibition of the synthesis and/or of the release of CGRP by sensitive nerve fibers.

In order for a chemical species to be recognized as a CGRP antagonist, it must in particular satisfy the following characteristic: it must have a CGRP antagonist pharmacological activity, i.e., induce a coherent pharmacological response, in particular in one of the following tests:

(a) the antagonist species must reduce the vasodilation induced by capsaicin, and/or (b) the antagonist species must induce an inhibition of the release of CGRP by sensitive nerve fibers, and/or (c) the antagonist species must reduce inhibition of the contraction of vas deferens smooth muscle induced by CGRP.

In addition, the antagonist may have an affinity for the CGRP receptors.

Hitherto, a link between CGRP and sensitive eyes had not been established.

CGRP 8-37 and anti-CGRP antibodies are suitable CGRP antagonists according to the invention.

In the compositions according to the invention, the CGRP antagonist is preferably employed in an amount ranging from 0.000001% to 10% by weight relative to the total weight of the composition, and in particular in an amount ranging from 0.0001% to 5% by weight relative to the total weight of the composition.

The CGRP antagonist may advantageously be combined with one or more antagonists of another neuropeptide such as substance P antagonists and/or one or more inflammation mediator antagonists such as histamine antagonists, interleukin 1 (IL1) antagonists and Tumor Necrosis Factor alpha (TNF alpha) antagonists.

The substance P antagonists are preferably receptor antagonists.

The substance P antagonists which are particularly well suited according to this invention are those described in published French patent application 94/05537, filed May 5, 1994 and assigned to the assignee hereof. Exemplary substance P antagonists include sendide and spantide II.

By way of example, the substance P antagonists and the inflammation mediator antagonists may be formulated in an amount constituting from 0.000001% to 10% of the total weight of the composition and, preferably, from 0.0001% to 5%.

Exemplary inflammation mediator antagonists according to the invention include diethylenediamine derivatives such as cinnarizine and cyclizine; aminopropane derivatives (dexchlorpheniramine, triprolidine); phenothiazine derivatives (alimemazine, promethazine); auranofin; lisophyline; A802715; sulfasalazine; cetirizine HCl; loratidine; esbatine; setastine HCl.

The compositions according to the invention may be formulated into any of the pharmaceutical forms normally employed for topical application; the subject compositions may, in particular, be in the form of aqueous, aqueous/alcoholic or oily solutions, or dispersions of the lotion or serum type, emulsions of liquid or semi-liquid consistency of the milk type, obtained by dispersion of a fatty phase in an aqueous phase (O/W) or conversely (W/O), or suspensions or emulsions of runny, semi-solid or solid consistency of the aqueous or anhydrous cream or gel type, microemulsions, microcapsules, microparticles, vesicle dispersions of ionic and/or nonionic type, or compacted or cast powders. These compositions are formulated according to conventional techniques.

For a topical application intended for therapeutic use, the subject compositions are advantageously in the form of a gel, a cream or an ointment for treating palpebral dysaesthesias and/or pains and/or pruritus and in the form of eye drops or eye washing solutions for treating ocular dysaesthesias and/or pains and/or pruritus.

For cosmetic applications, the subject compositions are advantageously formulated as protective or care creams for sensitive eyes, milks or lotions for cleansing or removing makeup from sensitive eyes and as makeup products for the eyes, in particular for sensitive eyes, such as eye pencils, mascaras, eyeliners and eye shadows.

The injectable compositions may be formulated as an aqueous or oily lotion, or in the form of a serum.

The compositions for oral administration may be formulated as wafer capsules, gelatin capsules, syrups or tablets.

The amounts of the various constituents of the compositions according to the invention are those used conventionally in the fields under consideration.

When the compositions of the invention are formulated as an emulsion, the proportion of the fatty phase advantageously ranges from 5% to 80% by weight, and preferably from 5% to 50% by weight, relative to the total weight of the composition. The oils, the emulsifying agents and the coemulsifying agents employed in the compositions in emulsion form are selected from among those used conventionally in the cosmetics and dermatological fields. The emulsifying agent and the coemulsifying agent are advantageously present in the compositions in a proportion ranging from 0.3% to 30% by weight, and preferably from 0.5% to 20% by weight, relative to the total weight of the composition. The emulsion may also contain lipid vesicles.

When the composition is an oily gel or solution, the amount of oil may constitute up to more than 90% by weight of the total weight of the composition.

In a known manner, the compositions of the invention may also contain additives and adjuvants common in such fields, such as hydrophilic or lipophilic gelling agents, hydrophilic or lipophilic active agents, preservatives, antioxidants, solvents, fragrances, fillers, sunscreens, odor absorbers, pigments and dyestuffs and colorants. The amounts of these various additives and adjuvants are those used conventionally in the fields under consideration and range, for example, from 0.01% to 10% of the total weight of the composition. Depending on their particular nature, these additives and adjuvants may be introduced into the fatty phase, into the aqueous phase and/or into lipid spherules.

Exemplary oils which are suitable for the compositions of the invention include mineral oils (liquid petrolatum), plant oils (liquid fraction of karite butter and sunflower oil), animal oils (perhydrosqualene), synthetic oils (purcellin oil), silicone oils (cyclomethicone) and fluoro oils (perfluoropolyethers). Fatty alcohols, fatty acids (stearic acid) or alternatively waxes (paraffin wax, carnauba wax or beeswax) may also be used.

Exemplary emulsifying agents according to the invention include glyceryl stearate, polysorbate 60 and the mixture of PEG-6/PEG-32/glycol stearate marketed under the trademark Tefose® 63 by Gattefosse.

Exemplary hydrophilic gelling agents which are suitable include carboxyvinyl polymers (carbomer), acrylic copolymers such as acrylate/alkylacrylate copolymers, polyacrylamides, polysaccharides such as hydroxypropylcellulose, natural gums and clays, and, as lipophilic gelling agents, representative thereof are the modified clays such as bentones, fatty acid metal salts such as aluminum stearates, hydrophobic silica, polyethylenes and ethylcellulose.

Exemplary hydrophilic active agents which may be incorporated include proteins or protein hydrolysates, amino acids, polyols, urea, allantoin, sugars and sugar derivatives, vitamins, starch and plant extracts, in particular Aloe vera extracts.

And exemplary lipophilic active agents which are suitable include tocopherol (vitamin E) and derivatives thereof, retinol (vitamin A) and derivatives thereof, essential fatty acids, ceramides and essential oils.

It is also intended, inter alia, to combine the CGRP antagonists with other active agents, in particular cicatrizing agents (for example vitamin $B_{12}$), antiseptics (for example boric acid), antiallergic agents (for example sodium cromoglycate), antiviral agents (for example acyclovir), anaesthetics (for example lidocaine hydrochloride and derivatives thereof) and nonsteroidal anti-inflammatory agents (for example indomethacin).

In order to further illustrate the present invention and the advantages thereof, the following specific examples are given, it being understood that same are intended only as illustrative and in nowise limitative.

In said examples to follow, all parts and percentages are given by weight.

EXAMPLE 1

Eye Drops

| | | |
|---|---|---|
| CGRP 8-37 | | 0.5% |
| Excipient: | qs | 100% |
| Sodium chloride | | |
| Sodium borate | | |
| Polysorbate 80 | | |
| Boric acid | | |
| Water | | |

EXAMPLE 2

Ointment

| | | |
|---|---|---|
| Anti-CGRP antibody | | 1% |
| Excipient: | qs | 100% |
| Benzalkonium chloride | | |
| Sodium edetate | | |
| D-mannitol | | |
| Carbomer | | |
| Sodium hydroxide | | |
| Water | | |

EXAMPLE 3

Solution

| | | |
|---|---|---|
| CGRP 8-37 | | 2% |
| Excipient: | | |
| Boric acid | | 5% |
| Sodium chloride | | 0.3% |
| Phenylmercuric borate | | 0.5% |
| Water | qs | 100% |

EXAMPLE 4

Ointment

The formulation of this example was identical to that of Example 2, except that it also contained 0.1% of sendide.

EXAMPLE 5

Eye Drops

The formulation of this example was identical to that of Example 2, except that it also contained 0.3% of loratidine.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for cosmetically making up and/or caring for the eyes, eyelashes and/or eyelids of a human subject, which obviates at least one of ocular pruritus, palpebral pruritus, ocular pain, palpebral pain, ocular dysaesthesia, and palpebral dysaesthesia, comprising topically applying thereto a cosmetically effective amount of at least one CGRP 8-37 or an anti-CGRP antibody, in a cosmetically acceptable medium therefor.

2. The method as defined by claim 1, comprising coadministering to said mammalian/human subject a therapeutically/cosmetically effective amount of at least one antagonist of a neuropeptide other than CGRP and/or at least one inflammation mediator antagonist.

3. The method as defined by claim 2, comprising coadministering to said mammalian/human subject at least one substance P antagonist, at least one histamine antagonist, at least one interleukin 1 antagonist and/or at least one TNF α antagonist.

4. The method as defined by claim 3, comprising coadministering to said mammalian/human subject at least one substance P antagonist.

5. The method as defined by claim 4, comprising coadministering to said mammalian/human subject at least one substance P receptor antagonist.

* * * * *